United States Patent [19]
Horn et al.

[11] Patent Number: 5,948,954
[45] Date of Patent: *Sep. 7, 1999

[54] HIGH STABILITY PEANUT

[75] Inventors: Michael Eugene Horn; Eric Jon Eikenberry; Juan Enrique Romero Lanuza, all of Madison, Wis.; James Douglas Sutton, Griffin, Ga.

[73] Assignees: Agrigenetics, Inc., San Diego, Calif.; Hershey Foods Corporation, Hershey, Pa.

[ * ] Notice: This patent is subject to a terminal disclaimer.

[21] Appl. No.: 08/948,794

[22] Filed: Oct. 10, 1997

Related U.S. Application Data

[63] Continuation of application No. 08/709,231, Sep. 3, 1996, Pat. No. 5,684,232, which is a continuation of application No. 08/363,499, Dec. 23, 1994, abandoned.

[51] Int. Cl.⁶ .............................. A01H 5/00; A01H 5/10; C12N 15/01; C12P 7/64
[52] U.S. Cl. .......................... 800/264; 800/270; 800/276; 800/298; 435/444
[58] Field of Search ..................................... 800/200, 230, 800/250, 255, DIG. 23, 69, 264, 270, 276, 298; 435/444

[56] References Cited

U.S. PATENT DOCUMENTS 5,684,232 11/1997 Horn et al. ............................. 800/200

FOREIGN PATENT DOCUMENTS 2617675 7/1988 France .

OTHER PUBLICATIONS

Bovi, M.L.A. (1982) "Genotypic and Environmental Effects on Fatty Acid Composition, Iodine Value, and Oil Content of Peanut (*Arachus Hypogaea* L.)" The University of Florida, Dissertation Abstracts International, p. 406 (**abstract only).

Norden et al. (1987) Peanut Science 14(1):7–11.

*Primary Examiner*—David T. Fox
*Attorney, Agent, or Firm*—Saliwanchik, Lloyd & Saliwanchik

[57] ABSTRACT

A commercially viable, runner-type peanut cultivar, as well as seeds and plants of the cultivar, agronomically similar to Florunner but having an improved fatty acid profile in the seed oil.

20 Claims, No Drawings

HIGH STABILITY PEANUT

This is a continuation, of application Ser. No. 08/709,231, filed Sep. 3, 1996, now U.S. Pat. No. 5,684,232; which is a continuation of Ser. No. 08/363,499, filed Dec. 23, 1994, now abandoned.

FIELD OF THE INVENTION

The present invention is directed to peanut varieties, plants, seeds, and oils wherein the seeds and oils have improved oxidative stability, increased shelf life, and enhanced sensory qualities, having application in both food and industrial applications.

More particularly, the present invention is directed to peanut varieties, plants, seeds, and oils wherein the seeds and oils have high levels of oleic acid.

DESCRIPTION OF BACKGROUND AND RELEVANT INFORMATION

The peanut plant is produced in many countries, and is recognized as one of the major oilseed crops and as a rich source of protein. Peanuts are grown worldwide in the tropic and temperate zones, and although they are grown elsewhere primarily for the seed oil, in the United States peanuts are used mainly for human foods such as peanut butter, roasted seeds, and confections. The United States is consistently a major exporter of peanuts for human consumption. The unique roasted flavor of peanuts is the basis for most marketing of export/import peanuts. Thus, improvement of the factors that indicate and/or affect food quality of peanuts is of considerable importance to the worldwide peanut processing and manufacturing community.

The performance characteristics of a plant oil, for either dietary or industrial purposes, are substantially determined by its fatty acid profile, that is, by the species of fatty acids present in the oil and the relative and absolute amounts of each species. The type and amount of unsaturation present in a plant oil has important consequences for both dietary and industrial applications. With regard to edible peanuts, their final quality is due principally to the chemical composition of the oil, protein, and carbohydrate fractions of the seed, with the oil component playing a major role. Other factors such as kernel size, blanching characteristics, roasted flavor, and shelf life also contribute to peanut quality.

Plant oils are subject to oxidative degradation, which can cause highly undesirable changes in color and odor, as well as detract from the lubricity and viscosity characteristics of the oil. Color and odor are of particular concern in food applications, where the autoxidation of oils, and the accompanying deterioration of flavor, is referred to as rancidity. The rate of oxidation is affected by several factors, including the presence of oxygen, exposure to light and heat, and the presence of native or added antioxidants and prooxidants in the oil. However, of most pertinence to the present invention, and perhaps generally, is the type and amount of unsaturation of the fatty acids in the oil.

By way of one example, peanut butter consists of a mixture of solid nut particles and liquid peanut oil. It is generally made by roasting and blanching raw peanut kernels, followed by grinding. The grinding operation breaks the cellular structure of the peanut kernels and liberates oil; the comminuted nut particles are suspended in this oil to form a product having a pasty and spreadable consistency.

An unavoidable side effect of the processing, and particularly the grinding, is the introduction of oxygen into the peanut butter. The presence of this oxygen promotes the development of rancidity; the oxygen oxidizes the peanut oil, causing the peanut butter to develop an undesirable taste and/or odor during prolonged storage, thereby reducing the useful shelf life of the peanut butter.

The fatty acids present in the peanut oil are not equally vulnerable to oxidation. Rather, the susceptibility of individual fatty acids to oxidation is dependent on their degree of unsaturation. Thus, the rate of oxidation of linolenic acid, which possesses three carbon-carbon double bonds, is 25–100 times that of oleic acid, which has only one double bond, and 2–10 times that of linoleic acid, which has two. Schultz, E. A. Day and R. O. Sinnhuber, *Symposium on Food Lipids and Their Oxidation,* AVI Publishing Co., Inc., London, England (1962). Linoleic and linolenic acids also have the most impact on flavor and odor because they readily form hydroperoxides. While saturated fatty acids are the most stable from the viewpoint of rancidity, they are highly undesirable from a health and nutrition viewpoint. Therefore, monounsaturated fatty acids present the best combination of nutritive and oxidative stability characteristics.

Resistance to oxidation can also have an important benefit before the peanut is crushed for oil or incorporated into a food product. There appears to be a correlation between susceptibility to oxidation and the formation of aflatoxin, an extremely undesirable contaminant which can result from the growth of certain molds. It has been reported that lipoperoxidation of the unsaturated fatty acids—particularly linolenic acid—in sunflower seeds appears to be involved in aflatoxin biosynthesis. Passi et al., "Role of lipoperoxidation in aflatoxin production," *Applied Microbiology* Biotechnology, pp. 186–190 (1984); Fanelli et al., 'Free radical and aflatoxin biosynthesis,"*Experientia,* 40:191–193 (1984). Therefore, peanuts whose oil contents are resistant to oxidation should also be resistant to aflatoxin formation.

The botanical classification of peanuts is subject to some apparent ambiguity, with sub-divisions being variously referred to as varieties, subvarieties, subspecies, classes, and types. Thus, commercial peanuts can be divided into at least two main botanical classes, Virginia and Spanish, and possibly a third, Valencia (Norden et al., "Breeding of the Cultivated Peanut," *Peanut Science and Technology* Ch. 4, pp. 95–121 (1982). Some sources use a different third main class, Runner (*Peanuts: Production, Processing, Products,* ch. 4, "The Culture of Peanuts," pp. 41 et seq., Woodroof, ed. (3d ed. 1983), while others appear to treat Runner as a sub-class of Virginia (Wynne et al., "Peanut Breeding," *Advances in Agronomy,* 34:39–72 (1981). (It appears that some of the apparent confusion may result from the use of overlapping nomenclature in taxonomic and commercial naming systems.) For purposes of the present discussion, Runner will be treated as a sub-class derived from the Virginia botanical class of peanut.

Virginia botanical types do not flower on the main stem and, in general terms, mature later, have a high water requirement, and are large-seeded. Spanish botanical types flower only on the main stem and, relative to Virginia types, mature earlier, have a lower water requirement, and have smaller seed.

Virginia peanuts are the more desirable for comestible applications, due to their generally superior size, texture, and taste compared to Spanish peanuts. In addition, oil from seeds of the different botanical types of peanuts differ in their tendency to develop oxidative rancidity and its associated undesirable odors and flavors. Virginia-type peanuts produce oil with a lower linoleic percentage, and therefore tend to have greater stability than Spanish types. Moreover, Virginia type peanut plants are superior to Spanish in several agronomic characteristics, including drought resistance, disease and pest resistance, and susceptibility to pod splitting.

In general, the genetic range of fatty acid compositions in peanuts is 41–67% oleic acid and 14–42% linoleic. O'Keefe et al., "Comparison of Oxidative Stability of High- and Normal-Oleic Peanut Oils," *J. Am. Oil Chem. Soc.*, 70:489–492 (1993), referencing Ahmed et al., *Peanut Science and Technology*, pp. 655–688 (1982). The Runner sub-class of Virginia-type peanut is the basis for the most widely used commercial peanut varieties in the United States, due to its excellent agronomic characteristics. A recent survey of Runner-type peanuts reported an oleic acid content range of 49.6–56.3%, and a linoleic acid content range of 24.1–30.6%. Branch et el., *J. Am. Oil Chem. Soc.*, 67:591 (1990).

One widely used commercial variety of the Runner sub-class is Florunner, which was introduced in the United States in 1969 as commercial runner type peanut derived from a cross between the varieties Early Runner and Florispan. Florunner constituted about 90% of all runner-type peanut grown in the U.S. in the 1970's, and still had about 70% of this market in 1992. Usage of Florunner in 1994 is estimated at between 60% and 70% of all runner-type peanut in the U.S., and 25 years after its introduction Florunner remains the most cultivated peanut trade variety in the United States, and is the standard against which every new introduction is measured. However, the oil of Florunner peanuts contains about 51% oleic fatty acid and 29% linoleic fatty acid, yielding an O/L ratio value of only about 1.76.

Prior attempts have been made to derive a high oleic/low linoleic variety having a Florunner background. Norden, French Patent Application No. 2,617,675, assigned to the University of Florida, describes a Florispan-derived peanut seed with an oil content of approximately 74–84% oleic acid and 2–8% linoleic acid. [This application claims priority from U.S. Ser. No. 071,881, filed Jul. 10, 1987, which does not appear to have issued as a U.S. patent.] However, the derivation of this peanut seed apparently included an early cross between a Virginia-type female parent and a Spanish-type male parent. This would be expected to yield offspring plants having substantially less desirable agronomic characteristics than a runner variety. Moreover, the seeds of such offspring would unavoidably reflect at least some of the inferior size, taste, and texture of Spanish peanuts; it appears, in fact, that they were classified as commercial Spanish-type peanuts under the U.S. Marketing System.

In a 1987 journal article, "Variability in Oil Quality Among Peanut Genotypes in the Florida Breeding Program," *Peanut Science*. 14:7–11, Norden et al. describe the lengthy efforts made by the Florida breeding program to improve the oil quality of *Arachis hypogaea* L. This paper was apparently a forerunner to filing of the above-referenced U.S. patent application. It describes the same two lines which form the basis of that application, 435-2-1 and 435-2-2, as being derived from seed stock which was a Florispan derivative, and acknowledges the possibility of a subsequent Spanish outcross based on "variation in seed characteristics."

In a follow-up to the Norden et al. work by Knauft et al., "Further Studies On The Inheritance of Fatty Acid Composition in Peanut," *Peanut Science*. 20:74–76 (1993), the authors, working from the F435 line, conclude that the high oleic acid trait in peanut follows simple genetic inheritance, such that "incorporation of high oleic acid into peanut cultivars should be straightforward." However, there is no acknowledgment that F435 is a Spanish genotype, and no recognition or discussion of whether the authors' conclusion, if accurate, would apply to incorporation of the high oleic acid trait into non-Spanish backgrounds. Given the commercial dominance of runner-derived peanut lines, the current peanut production system, and the need to maintain the existing agronomic and flavor characteristics of the premium commercial varieties, introgression breeding of the high O/L trait from other varieties into Florunner is a difficult and uncertain approach which is unlikely to be commercially feasible.

It would, therefore, be particularly beneficial to develop a variety of Virginia-type peanut having the desirable agronomic characteristics of the Runner class, and in particular the Florunner variety, yet also having oil with a high content of monounsaturated acids and a low content of saturated and polyunsaturated fatty acids. The superior oxidative stability of oil from such a peanut variety would provide benefits in both industrial and comestible uses, where increased shelf life would decrease the incidence of rancidity and improve product quality, not only of the oil per se, but also of food products containing the peanuts in whole or reduced form.

Moreover, there would be very substantial practical benefits if a commercial high oleic peanut line was made available having agronomic characteristics substantially identical to those of Florunner. Because of the long-standing dominance of Florunner, every step in the chain of peanut production and marketing is highly calibrated to handling peanuts and peanut products having Florunner characteristics. Growers would be receptive to such a variety because they would know what to expect in matters such as yield, disease and pest resistance, and harvesting factors such as the plant growth habit, pod size and placement on the plant, and the incidence of hull splitting. Hulling and crushing could also be carried out with little or no adjustment to machine set-up and process parameters (cracking force, blanching conditions, incidence of split peanuts), as well as with a reasonable expectation of yield. Wholesalers, retailers, and end users would be highly receptive to peanut products whose only substantial distinguishing characteristic in comparison to Florunner was a dramatically improved fatty acid content

SUMMARY OF THE INVENTION

The present invention provides a variety of Virginia-type peanut having the desirable agronomic characteristics of the Runner class of peanut. This variety further provides oil having a high content of monounsaturated acids and a low content of saturated and polyunsaturated fatty acids. This oil composition provides superior oxidative stability, which is of benefit in industrial and comestible uses. The invention also provides a method for producing peanut plants having seed with an advantageous phenotype of desirable agronomic characteristics, coupled with a favorable oil composition including high oleic acid content by treating Virginia-type Runner peanut seed with an alkylating mutagen such as ethyl methane sulfonate, growing the treated seed into plants, analyzing the fatty acid content of seeds from those plants and selecting those having the desired fatty acid profile for further culturing.

DETAILED DESCRIPTION OF THE PREFERRED EMBODIMENTS

A. 1992 Georgia Mutagenesis Nursery

In May of 1992, two lots of Florunner seed (*Arachis hypogaea* L. var. 'Florunner'), designated Lots C and D, were treated with ethylmethanesulfonate (EMS) as follows:

| Lot | Mutagen Treatment | Seed Treated | Planting Date |
|---|---|---|---|
| C | EMS 1.5% (v/v) 6 hours | 15 lbs (12,000 seeds) | May 7 |
| D | EMS 1.5% (v/v) 7 hours | 12 lbs (10,000 seeds) | May 8 |

The seeds were imbibed with water overnight prior to the treatment with EMS. After soaking in the EMS solution for the time indicated, the EMS solution was quenched to cease mutagenic activity and the seed was rinsed with running water overnight. The following morning, the resulting M1 seeds were planted in a 1 acre field nursery near Perry, Ga., and the nursery site was irrigated right after planting. Controls were also planted along with the EMS treated M1 seed. (As used herein, M1 seed is the seed originally subjected to mutagenesis; when planted, it gives rise to M1 plants, which produce M2 seed; the M2 seed grows into M2 plants, which bear M3 seed; and so on.)

Approximately 1,710 and 1,895 M1 plants from Lots C and D, respectively, emerged in these Georgia plantings, giving an overall emergence frequency of only 18–19%, substantially lower than the 50% target. The untreated Florunner controls had 95% emergence. About 75–80% of the plants from the EMS treatments were reasonably normal, the other 20–25% having various abnormalities including stunting, yellowing, and wilting.

In November 1992, the approximately 3,600 surviving M1 plants from Lots C and D (of the emerging 3,605) and a representative sample of the Florunner controls were harvested, the pods were dried at 35° C. for 3 days and the seed harvested from each M1 plant was processed as follows:

- a) 10 seeds from 5 pods of adequate maturity (based on the shake test) were sent to Puerto Rico for planting in a winter nursery, resulting in 3,600 nursery rows;
- b) 10 seeds from 5 pods of complete maturity (based on the hull scrape test) were sent to Madison, Wis. for bulk and half-seed fatty acid analysis (some M1 plants did not produce completely mature seed and thus could not be analyzed for fatty acid composition); and
- c) the remnant seed was retained for backup.

The hull scrape test is well known to those in the art, and is described in Baldwin, J., "The Hull Scrape Method to Assess Peanut Maturity," Bulletin 958, Co-operative Extension Service, Univ. of Georgia College of Agriculture (1990). The shake test is similarly well known, and involves shaking selected pods; if the seeds rattle in the pods, the peanuts are considered to have adequate maturity for shelling.

B. Analysis of M2 Seed from the 1992 Mutagenesis Nursery

Fatty acid analyses of the completely mature seeds was carried out during the winter of 1992–93. The 10 M2 seeds per M1 plant were first analyzed as two, 5-seed bulks. M2 half-seeds were then analyzed in those bulks (about 10%) with the lowest levels of linoleic acid, the highest levels of oleic acid, and the highest O/L ratio.

In analyzing for oleic acid levels, fatly acid composition can be determined by gas liquid chromatography (GLC) in accordance with standard procedures. GLC analysis can be conducted on a 3–6 seed bulk sample, and/or on a single seed basis, and/or on a one-half seed sample; this latter technique allows the planting of the remaining half-seed, which contains the embryo, for further breeding. The analysis involves first extracting the oil from the seed, and converting the fatty acid content to methyl esters. The resulting methyl esters are analyzed for fatty acid content by GLC, which separates the fatty acids on the basis of their degree of unsaturation and carbon chain length. This analysis is performed by means well known in the art, such as, e.g., McCreary, D. K. et al., *J. Chromatog. Sci.* 16:329–331 (1978).

These analyses resulted in the identification of a number of putative fatty acid variants in Lots C and D, most notably plant 458 of Lot C (hereinafter "C458"). Analyses of M2 half-seeds from M1 plant C458 resulted in the identification of a number of additional low linoleic/high oleic individuals, for which the proportions of linoleate ranged from 2.0–2.8% (for seven individuals; one additional half-seed contained 15.8% linoleate, which was still considerably lower than the control value of 26.7%).

C. 1992–93 Puerto Rico M2 Nursery

The Puerto Rico M2 nursery was planted near Ponce in November 1992 to take advantage of the 1992–93 winter growing season. Emergence was 70% on average, i.e., 7 plants per M2 progeny row out of 10 seeds planted. In late April 1993, the nursery was harvested. All M2 plants were harvested in those nursery rows corresponding to the putative M2 half-seed fatty acid variants identified in the analyses of M2 seed at Madison over the winter of 1992–93. Particular attention was given to the row corresponding to C458; agronomic, phenotypic, yield and fatty acid data were collected for this row and the two adjacent Florunner rows for comparison purposes. In addition, all M2 plants were harvested in those rows for which there had not been any mature M2 seed for analysis at Madison over the winter of 1992–93.

The results obtained from the 1992–93 Puerto Rico nursery indicated that the fatty acid variant C458 had agronomic and yield performance comparable to Florunner and that it was phenotypically indistinguishable from the adjacent Florunner nursery rows. The only detectable difference was in the fatty acid composition of the seed lipids.

More specifically, the harvest of M2 plants from the 1992–93 Puerto Rico planting included eight plants grown from M2 seed of the original M1 C458 plant. These eight plants were designated C458-1 through C-458-8. Two M3 seeds from each plant were harvested on Mar. 29, 1993, and two more seeds from each plant were harvested on Apr. 28, 1993. The resulting fatty acid analyses, as well as the yields, appear in Table 1.

This analysis identified C458-2 and C458-7 as questionable. C458-2 exhibited a wild-type oil profile and was not investigated further, while C458-7 appeared to show segregation. In addition, M2 plant C458-8 had poor seed quality.

The control rows adjacent to the row of M2 C458 plant in Puerto Rico, rows C457 and C459, were found to have fatty acid profiles substantially similar to that of Florunner (Table 2).

TABLE 1

Fatty Acid Profiles of M3 Half-seeds and Seed Yields of C458; 1992–93 Puerto Rico Nursery

| Plant | Seed | 16:0 | 16:1 | 18:0 | 18:1 | 18:2 | 18:3 | 20:0 | 20:1 | 22:0 | 22:1 | 24:0 | O/L | Sats | Yield Grams | Yield Seeds |
|---|---|---|---|---|---|---|---|---|---|---|---|---|---|---|---|---|
| C458-1 | 1 | 6.4 | 0.1 | 2.2 | 76.1 | 6.2 | 0.2 | 1.1 | 2.6 | 2.9 | 0.4 | 1.9 | 12.3 | 14.5 | | |
|  | 2 | 6.2 | 0.1 | 2.1 | 76.0 | 5.8 | 0.1 | 1.1 | 2.8 | 3.3 | 0.4 | 2.0 | 13.1 | 14.7 | | |
|  | 3 | 6.5 | 0.1 | 2.2 | 78.9 | 3.8 | 0.1 | 1.1 | 2.3 | 3.1 | 0.0 | 1.8 | 20.8 | 14.7 | | |
|  | 4 | 6.7 | 0.1 | 2.3 | 78.3 | 3.8 | 0.1 | 1.1 | 2.3 | 3.1 | 0.2 | 1.9 | 20.6 | 15.2 | | |
|  | Avg | 6.5 | 0.1 | 2.2 | 77.3 | 4.9 | 0.1 | 1.1 | 2.5 | 3.1 | 0.3 | 1.9 | 16.7 | 14.8 | 93.0 | 252.0 |
| C458-2 | 1 | 10.3 | 0.1 | 1.7 | 41.4 | 37.0 | 0.2 | 1.1 | 1.9 | 3.9 | 0.2 | 2.3 | 1.1 | 19.3 | | |
|  | 2 | 10.3 | 0.1 | 1.7 | 41.3 | 36.8 | 0.2 | 1.1 | 1.9 | 4.0 | 0.2 | 2.4 | 1.1 | 19.5 | | |
|  | 3 | 10.0 | 0.1 | 2.2 | 47.0 | 32.9 | 0.1 | 1.2 | 1.5 | 3.1 | 0.1 | 1.8 | 1.4 | 18.3 | | |
|  | 4 | 10.2 | 0.1 | 2.4 | 48.5 | 31.2 | 0.1 | 1.3 | 1.4 | 3.0 | 0.1 | 1.7 | 1.6 | 18.6 | | |
|  | Avg | 10.2 | 0.1 | 2.0 | 44.6 | 34.5 | 0.2 | 1.2 | 1.7 | 3.5 | 0.2 | 2.1 | 1.3 | 18.9 | 122.5 | 190.0 |
| C458-3 | 1 | 5.4 | 0.1 | 2.2 | 79.7 | 3.4 | 0.1 | 1.2 | 2.3 | 3.1 | 0.2 | 2.2 | 23.4 | 14.1 | | |
|  | 2 | 5.3 | 0.1 | 2.8 | 78.5 | 3.6 | 0.2 | 1.4 | 2.4 | 3.2 | 0.3 | 2.2 | 21.8 | 14.9 | | |
|  | 3 | 5.7 | 0.1 | 2.5 | 79.3 | 3.8 | 0.1 | 1.2 | 2.4 | 2.8 | 0.3 | 1.9 | 20.9 | 14.1 | | |
|  | 4 | 5.6 | 0.2 | 2.5 | 80.4 | 3.1 | 0.1 | 1.2 | 2.2 | 2.7 | 0.2 | 1.9 | 25.9 | 13.9 | | |
|  | Avg | 5.5 | 0.1 | 2.5 | 79.5 | 3.5 | 0.1 | 1.3 | 2.3 | 3.0 | 0.3 | 2.1 | 23.0 | 14.3 | 79.4 | 121.0 |
| C458-4 | 1 | 5.5 | 0.1 | 1.4 | 79.4 | 3.9 | 0.1 | 0.9 | 2.9 | 3.1 | 0.3 | 2.2 | 20.4 | 13.1 | | |
|  | 2 | 5.5 | 0.1 | 1.7 | 79.5 | 3.5 | 0.1 | 1.1 | 2.7 | 3.2 | 0.3 | 2.3 | 22.7 | 13.8 | | |
|  | 3 | 5.7 | 0.1 | 1.9 | 80.4 | 3.4 | 0.1 | 1.0 | 2.4 | 2.8 | 0.3 | 2.0 | 23.6 | 13.4 | | |
|  | 4 | 5.6 | 0.1 | 1.9 | 79.7 | 4.0 | 0.1 | 1.0 | 2.6 | 3.0 | 0.0 | 2.0 | 19.9 | 13.5 | | |
|  | Avg | 5.6 | 0.1 | 1.7 | 79.8 | 3.7 | 0.1 | 1.0 | 2.7 | 3.0 | 0.3 | 2.1 | 21.6 | 13.5 | 59.0 | 147.0 |
| C458-5 | 1 | 5.2 | 0.1 | 1.7 | 80.5 | 2.8 | 0.2 | 1.2 | 2.6 | 3.2 | 0.3 | 2.3 | 28.8 | 13.6 | | |
|  | 2 | 5.4 | 0.1 | 1.5 | 80.5 | 3.2 | 0.1 | 1.0 | 2.6 | 3.0 | 0.3 | 2.3 | 25.2 | 13.2 | | |
|  | 3 | 5.5 | 0.1 | 1.9 | 81.1 | 3.1 | 0.1 | 1.1 | 2.2 | 2.8 | 0.2 | 2.0 | 26.2 | 13.3 | | |
|  | 4 | 5.5 | 0.1 | 1.9 | 80.5 | 3.2 | 0.1 | 1.1 | 2.4 | 2.9 | 0.3 | 2.1 | 25.2 | 13.5 | | |
|  | Avg | 5.4 | 0.1 | 1.8 | 80.7 | 3.1 | 0.1 | 1.1 | 2.5 | 3.0 | 0.3 | 2.2 | 26.3 | 13.4 | 115.7 | 165.0 |
| C458-6 | 1 | 5.4 | 0.1 | 1.3 | 80.4 | 3.3 | 0.1 | 0.9 | 2.8 | 3.1 | 0.3 | 2.2 | 24.4 | 12.9 | | |
|  | 2 | 5.2 | 0.1 | 1.2 | 80.6 | 3.6 | 0.2 | 0.9 | 2.8 | 2.9 | 0.3 | 2.1 | 22.4 | 12.3 | | |
|  | 3 | 6.2 | 0.2 | 2.5 | 78.6 | 3.4 | 0.1 | 1.4 | 2.2 | 3.3 | 0.2 | 2.1 | 23.1 | 15.5 | | |
|  | 4 | 6.7 | 0.2 | 1.9 | 79.3 | 3.3 | 0.0 | 1.1 | 2.2 | 2.9 | 0.2 | 2.1 | 24.0 | 14.7 | | |
|  | Avg | 5.9 | 0.2 | 1.7 | 79.7 | 3.4 | 0.1 | 1.1 | 2.5 | 3.1 | 0.3 | 2.1 | 23.5 | 13.9 | 56.7 | 98.0 |
| C458-7 | 1 | 5.7 | 0.1 | 1.3 | 79.8 | 4.1 | 0.1 | 0.8 | 2.9 | 2.7 | 0.4 | 2.1 | 19.5 | 12.6 | | |
|  | 2 | 9.0 | 0.1 | 1.8 | 55.6 | 24.9 | 0.1 | 1.0 | 2.1 | 3.2 | 0.2 | 2.0 | 2.2 | 17.0 | | |
|  | 3 | 9.4 | 0.1 | 2.4 | 59.0 | 22.3 | 0.0 | 1.1 | 2.0 | 3.4 | 0.2 | 0.0 | 2.6 | 16.3 | | |
|  | 4 | 9.5 | 0.1 | 2.3 | 57.2 | 22.7 | 0.0 | 1.2 | 1.9 | 3.1 | 0.2 | 1.9 | 2.5 | 18.0 | | |
|  | Avg | 8.4 | 0.1 | 2.0 | 62.9 | 18.5 | 0.1 | 1.0 | 2.2 | 3.1 | 0.3 | 2.0 | 6.7 | 16.0 | 152.0 | 239.0 |
| C458-8 | 1 | 6.8 | 0.1 | 2.2 | 74.1 | 5.6 | 0.1 | 1.3 | 2.7 | 4.2 | 0.3 | 2.3 | 13.2 | 16.8 | | |
|  | 2 | 6.7 | 0.1 | 2.4 | 74.6 | 6.0 | 0.1 | 1.3 | 2.7 | 3.7 | 0.4 | 2.1 | 12.4 | 16.2 | | |
|  | 3 | 7.5 | 0.1 | 2.7 | 74.0 | 5.8 | 0.0 | 1.4 | 2.3 | 3.7 | 0.3 | 2.1 | 12.8 | 17.4 | | |
|  | 4 | 7.1 | 0.1 | 2.1 | 77.1 | 4.6 | 0.0 | 1.2 | 2.4 | 3.1 | 0.3 | 2.0 | 16.8 | 15.5 | | |
|  | Avg | 7.0 | 0.1 | 2.4 | 75.0 | 5.5 | 0.1 | 1.3 | 2.5 | 3.7 | 0.3 | 2.1 | 13.8 | 16.5 | 24.9 | 93.0 |

Seeds 1 & 2 harvested March 29
Seeds 3 & 4 harvested April 28

TABLE 2

Fatty Acid Profiles of M3 Half-seeds and Seed Yields for C457 and C459; 1992–93 Puerto Rico Nursery

| Plant | Seed | GC | 16:0 | 16:1 | 18:0 | 18:1 | 18:2 | 18:3 | 20:0 | 20:1 | 22:0 | 22:1 | 24:0 | O/L | Sats | Yld (gm) |
|---|---|---|---|---|---|---|---|---|---|---|---|---|---|---|---|---|
| 457-1 | 1 | 1 | 9.4 | 0.1 | 2.8 | 53.2 | 26.9 | 0.1 | 1.4 | 1.4 | 3.0 | 0.1 | 1.7 | 2.0 | 18.2 | 83.9 |
|  | 2 | 2 | 9.9 | 0.1 | 1.7 | 47.9 | 32.6 | 0.1 | 1.0 | 1.6 | 3.0 | 0.2 | 1.8 | 1.5 | 17.4 | |
| 457-2 | 1 | 3 | 9.8 | 0.1 | 2.1 | 51.6 | 29.4 | 0.1 | 1.3 | 1.7 | 3.8 | 0.2 | 0.0 | 1.8 | 17.0 | 83.9 |
|  | 2 | 4 | 9.9 | 0.1 | 1.9 | 46.1 | 33.8 | 0.1 | 1.2 | 1.6 | 3.2 | 0.2 | 1.9 | 1.4 | 18.1 | |
| 457-3 | 1 | 5 | 9.6 | 0.1 | 2.4 | 49.6 | 29.9 | 0.1 | 1.3 | 1.5 | 3.5 | 0.1 | 1.9 | 1.7 | 18.8 | 83.9 |
|  | 2 | 6 | 9.8 | 0.1 | 2.7 | 50.1 | 29.7 | 0.1 | 1.4 | 1.4 | 3.0 | 0.1 | 1.7 | 1.7 | 18.6 | |
| 457-4 | 1 | 7 | 10.5 | 0.1 | 2.4 | 47.1 | 33.8 | 0.0 | 1.3 | 1.4 | 3.1 | 0.1 | 0.0 | 1.4 | 17.4 | 97.5 |
|  | 2 | 8 | 10.0 | 0.1 | 2.2 | 44.2 | 35.2 | 0.0 | 1.3 | 1.5 | 3.4 | 0.1 | 1.9 | 1.3 | 18.8 | |
| 457-5 | 1 | 9 | 10.3 | 0.1 | 1.7 | 47.7 | 33.6 | 0.0 | 1.1 | 1.8 | 3.5 | 0.2 | 0.0 | 1.4 | 16.6 | 63.5 |
|  | 2 | 10 | 11.1 | 0.1 | 2.3 | 48.6 | 34.7 | 0.1 | 1.2 | 1.8 | 0.0 | 0.2 | 0.0 | 1.4 | 14.6 | |
| 457-6 | 1 | 11 | 10.8 | 0.1 | 2.1 | 48.3 | 32.3 | 0.1 | 1.1 | 1.6 | 3.5 | 0.1 | 0.0 | 1.5 | 17.5 | 104.3 |
|  | 2 | 12 | 10.5 | 0.1 | 2.1 | 47.2 | 31.9 | 0.1 | 1.2 | 1.5 | 3.4 | 0.1 | 1.8 | 1.5 | 19.0 | |
| 457-7 | 1 | 13 | 10.3 | 0.1 | 2.0 | 46.1 | 33.4 | 0.1 | 1.2 | 1.6 | 3.0 | 0.1 | 2.2 | 1.4 | 18.6 | 86.2 |
|  | 2 | 14 | 10.1 | 0.1 | 2.3 | 49.3 | 32.4 | 0.1 | 1.3 | 1.5 | 2.9 | 0.1 | 0.0 | 1.5 | 16.5 | |
| 457 | Avg | | 10.1 | 0.1 | 2.2 | 48.4 | 32.1 | 0.1 | 1.2 | 1.6 | 3.3 | 0.1 | 1.9 | 1.5 | 17.7 | 86.2 |
| 459-1 | 1 | 15 | 9.7 | 0.1 | 1.7 | 45.5 | 33.6 | 0.1 | 1.0 | 2.1 | 3.8 | 0.2 | 2.2 | 1.4 | 18.4 | 31.8 |
|  | 2 | 16 | 10.1 | 0.1 | 1.7 | 43.1 | 35.7 | 0.0 | 1.0 | 2.0 | 4.0 | 0.0 | 2.2 | 1.2 | 19.1 | |
| 459-2 | 1 | 17 | 10.0 | 0.1 | 2.0 | 48.4 | 32.5 | 0.1 | 1.1 | 1.3 | 2.7 | 0.1 | 1.6 | 1.5 | 17.4 | 83.9 |
|  | 2 | 18 | 10.1 | 0.1 | 1.6 | 46.2 | 32.7 | 0.1 | 1.1 | 1.9 | 3.9 | 0.2 | 2.2 | 1.4 | 18.7 | |

TABLE 2-continued

Fatty Acid Profiles of M3 Half-seeds and Seed Yields for C457 and C459;
1992–93 Puerto Rico Nursery

| Plant | Seed | GC | 16:0 | 16:1 | 18:0 | 18:1 | 18:2 | 18:3 | 20:0 | 20:1 | 22:0 | 22:1 | 24:0 | O/L | Sats | Yld (gm) |
|---|---|---|---|---|---|---|---|---|---|---|---|---|---|---|---|---|
| 459-3 | 1 | 19 | 9.3 | 0.1 | 1.8 | 48.5 | 31.9 | 0.1 | 1.1 | 1.7 | 3.3 | 0.2 | 2.0 | 1.5 | 17.6 | 113.4 |
|  | 2 | 20 | 10.6 | 0.1 | 1.8 | 44.5 | 36.1 | 0.1 | 1.1 | 1.8 | 3.8 | 0.2 | 0.0 | 2.2 | 17.3 |  |
| 459-4 | 1 | 21 | 9.7 | 0.1 | 2.1 | 46.6 | 32.9 | 0.1 | 1.2 | 1.7 | 3.4 | 0.2 | 2.0 | 1.4 | 18.4 | 63.5 |
|  | 2 | 22 | 10.5 | 0.1 | 2.2 | 47.8 | 32.9 | 0.1 | 1.1 | 1.7 | 3.3 | 0.2 | 0.0 | 1.5 | 17.2 |  |
| 459-5 | 1 | 23 | 9.8 | 0.1 | 1.9 | 48.6 | 31.8 | 0.1 | 1.1 | 1.5 | 3.0 | 0.1 | 1.9 | 1.5 | 17.7 | 70.3 |
|  | 2 | 24 | 9.8 | 0.1 | 2.0 | 47.9 | 31.6 | 0.1 | 1.2 | 1.6 | 3.5 | 0.1 | 2.0 | 1.5 | 18.5 |  |
| 459-6 | 1 | 25 | 10.5 | 0.1 | 2.3 | 46.3 | 32.5 | 0.0 | 1.2 | 1.6 | 3.5 | 0.2 | 1.8 | 1.4 | 19.3 | 43.1 |
|  | 2 | 26 | 11.1 | 0.1 | 3.3 | 45.9 | 32.1 | 0.1 | 1.5 | 1.2 | 3.1 | 0.1 | 1.6 | 1.4 | 20.6 |  |
| 459-7 | 1 | 27 | 10.0 | 0.1 | 1.9 | 44.1 | 35.9 | 0.1 | 1.1 | 1.5 | 3.2 | 0.2 | 1.9 | 1.2 | 18.2 | 68.0 |
|  | 2 | 28 | 10.5 | 0.2 | 2.0 | 49.7 | 32.8 | 0.1 | 1.2 | 1.5 | 0.0 | 0.2 | 1.9 | 1.5 | 15.6 |  |
| 459 | Avg |  | 10.1 | 0.1 | 2.0 | 46.7 | 33.2 | 0.1 | 1.2 | 1.7 | 3.4 | 0.2 | 1.9 | 1.4 | 18.1 | 67.7 |
| Average |  |  | 10.1 | 0.1 | 2.1 | 47.5 | 32.7 | 0.1 | 1.2 | 1.6 | 3.1 | 0.2 | 1.4 | 1.5 | 17.9 | 76.9 |

Seeds 1 and 2 harvested April 28

1992–93 M2 Half-seed Greenhouse Growouts

In addition to the Puerto Rico planting, the non-analyzed portion of the M2 half-seeds of the putative variants from Lots C and D were planted in the Madison greenhouses in the winter of 1992–93. The plants grown from those half-seeds were harvested in September–October 1993, and the resulting mature M3 seed was analyzed. This analysis confirmed that, from the original 22,000 treated seeds and resultant 3,605 emergent plants, only variants C458 and D596-3 had substantially reduced levels of linoleic acid, increased levels of oleic acid, and increased O/L ratios. A third variant, D398, was very weak and had intermediate levels of oleic and linoleic acid with only a small increase in O/L ratio. The other putative variants did not prove to be significantly different from the wild type in heir M3 seed progenies.

3) half-seeds produced from remnant M2 seed of C458.

In mid November, the C458 nursery at Hollinville was harvested and yield data was collected for the C458 selections. Fatty acid analyses were performed on two mature seeds from each M3 plant of the M2 selections C458-1, -3, -4, -5, -6, and -8 (Table 3).

The results obtained from the C458 nursery indicated that C458 selections 1, 3, 5, and 6 demonstrated the best yield performance, which was only somewhat lower than that of Florunner. C458 selections 1, 3, 4, 5, 6 and 8 were stable for the mutant fatty acid profile, and had average oleic acid levels of about 81% with less than 4% linoleic acid (O/L ratio>20).

TABLE 3

C458 (M3 Plants, M4 Seed);
1993 Georgia Nursery

| Genotype | # Sein | 16:0 | 16:1 | 18:0 | 18:1 | 18:2 | 18:3 | 20:0 | 20:1 | 22:0 | 22:1 | 24:0 | O/L | Sats |
|---|---|---|---|---|---|---|---|---|---|---|---|---|---|---|
| C458-1 | 77 | 5.2 | 0.0 | 1.1 | 80.5 | 4.6 | 0.1 | 1.0 | 2.8 | 2.6 | 0.4 | 1.7 | 17.5 | 11.6 |
| C458-3 | 35 | 5.1 | 0.1 | 1.9 | 82.4 | 3.3 | 0.1 | 1.0 | 2.5 | 2.6 | 0.3 | 0.7 | 25.0 | 11.3 |
| C458-4 | 79 | 5.0 | 0.1 | 1.7 | 81.0 | 3.7 | 0.1 | 0.9 | 2.9 | 2.8 | 0.4 | 1.4 | 21.9 | 11.8 |
| C458-5 | 81 | 5.1 | 0.1 | 2.0 | 81.0 | 3.3 | 0.1 | 1.1 | 2.7 | 2.8 | 0.3 | 1.5 | 24.5 | 12.5 |
| C458-6 | 53 | 4.9 | 0.1 | 1.7 | 81.2 | 3.3 | 0.1 | 1.0 | 2.8 | 2.7 | 0.4 | 1.8 | 24.6 | 12.1 |
| C458-8 | 31 | 5.0 | 0.1 | 1.8 | 79.0 | 4.6 | 0.1 | 1.1 | 3.3 | 3.0 | 0.5 | 1.5 | 11.2 | 12.4 |
| C458 avg | 356 | 5.1 | 0.1 | 1.7 | 80.9 | 3.8 | 0.1 | 1.0 | 2.8 | 2.8 | 0.4 | 1.4 | 21.8 | 12.0 |

Analysis of all M3 seed from the intermediate C458 M2 half-seed #2 indicated that the variation for reduced linoleic acid in C458 is controlled by a single gene, and that the inheritance of the trait is additive or co-dominant in phenotypic expression (1:2:1 segregation).

E. 1993 Georgia M3 Nurseries

In May 1993, a peanut nursery site was planted in Hollinville, Ga. with the following materials:

1) C458 M3 progeny rows planted with seed harvested from the single M2 plants in the C458 Puerto Rico nursery row;

2) cuttings from the C458, D596-3, and other putative half-seed M2 variants growing in the Madison greenhouses; and F. 1993–94 Puerto Rico Increase M4 seed from the 1993 Georgia nursery was planted in Puerto Rico and grown over the 1993–94 winter growing season. This seed consisted of seed from the C458-1, -3, -4, -5, -6, and -8 genotypes, as well as seed from the D596-3 genotype first identified in the 1992–93 M2 half-seed greenhouse growouts. (The D596-3 seed from the greenhouse grow-outs had been planted in progeny rows in the field in Georgia in 1993; it was decided that there was insufficient seed from these rows for fatty acid analysis, and all of the resulting seed was accordingly planted in Puerto Rico for increase over the 1993–94 season.) Mature M5 seed was harvested from the resulting M4 plants and analyzed for fatty acid composition; the results appear in Table 4A.

TABLE 4A

Fatty Acid Profiles of M5 Half-seeds for C458 and D596-3; 1993–94 Puerto Rico Nursery

| Genotype | # of plants | 16:0 | 16:1 | 18:0 | 18:1 | 18:2 | 18:3 | 20:0 | 20:1 | 22:0 | 22:1 | 24:0 | O/L | Sats |
|---|---|---|---|---|---|---|---|---|---|---|---|---|---|---|
| C458-1 | 1200 | 6.0 | 0.1 | 1.8 | 80.5 | 3.4 | 0.1 | 1.0 | 2.3 | 2.7 | 0.2 | 1.9 | 23.7 | 13.4 |
| C458-3 | 470 | 6.0 | 0.0 | 1.7 | 81.1 | 3.5 | 0.1 | 1.0 | 2.4 | 2.9 | 0.2 | 1.1 | 23.2 | 12.7 |
| C458-4 | 1145 | 6.0 | 0.1 | 1.7 | 80.3 | 3.6 | 0.1 | 1.0 | 2.4 | 2.8 | 0.3 | 1.7 | 22.3 | 13.2 |
| C458-5 | 1360 | 6.1 | 0.1 | 1.9 | 80.8 | 3.3 | 0.1 | 1.1 | 2.3 | 2.8 | 0.2 | 1.3 | 24.5 | 13.2 |
| C458-6 | 795 | 6.0 | 0.1 | 1.6 | 80.8 | 3.8 | 0.1 | 1.0 | 2.5 | 2.9 | 0.3 | 0.9 | 21.3 | 12.4 |
| C458-8 | 1170 | 6.1 | 0.0 | 1.9 | 80.8 | 3.5 | 0.1 | 1.0 | 2.3 | 2.5 | 0.3 | 1.5 | 23.1 | 13.0 |
| C458 avg | | 6.0 | 0.1 | 1.8 | 80.7 | 3.5 | 0.1 | 1.0 | 2.4 | 2.8 | 0.3 | 1.4 | 23.0 | 13.0 |
| D596-3 | 405 | 6.0 | 0.1 | 1.9 | 80.2 | 4.2 | 0.1 | 1.1 | 2 | 2.6 | 0.1 | 1.7 | 19.1 | 13.3 |

A comparison of fatty acid profiles as among the three main size classes of peanut—#1, Medium, and Jumbo—from the 1993–94 Puerto Rico Nursery is provided in Table 4B.

the methods described by Bigalli, G., "Usefulness and Limitations of Fatty Acids Distribution Determination in the Confectionery Industry," *HFC Food Sci. & Techn.*, 35th P.M.C.A. Production Conference, pp. 82–86 (1981).

TABLE 4B

1993–94 Puerto Rico Increase (By Seed Size)

| Cultivar | Seed size | Sample | 16:0 | 16:1 | 18:0 | 18:1 | 18:2 | 18:3 | 20:0 | 20:1 | 22:0 | 22:1 | 24:0 | O/L | Sats | 20+ | 20:0+ | XX:1 |
|---|---|---|---|---|---|---|---|---|---|---|---|---|---|---|---|---|---|---|
| C458-1 | #1 | 1 | 6.3 | 0.1 | 1.8 | 79.8 | 3.7 | 0.0 | 1.0 | 2.4 | 2.7 | 0.3 | 1.8 | 21.6 | 13.6 | 8.2 | 5.5 | 82.6 |
| | #1 | 2 | 6.3 | 0.3 | 1.9 | 79.0 | 4.0 | 0.2 | 1.0 | 2.3 | 2.8 | 0.3 | 1.8 | 19.8 | 13.8 | 8.2 | 5.6 | 81.9 |
| | Medium | 1 | 6.1 | 0.1 | 1.8 | 80.0 | 3.6 | 0.3 | 1.0 | 2.3 | 2.7 | 0.2 | 1.8 | 22.2 | 13.4 | 8.0 | 5.5 | 82.6 |
| | Medium | 2 | 6.1 | 0.1 | 1.8 | 80.0 | 3.8 | 0.1 | 1.0 | 2.3 | 2.7 | 0.2 | 1.8 | 21.1 | 13.4 | 8.0 | 5.5 | 82.6 |
| | Jumbo | 1 | 5.8 | 0.1 | 1.9 | 81.3 | 3.0 | 0.1 | 1.1 | 2.1 | 2.5 | 0.2 | 1.8 | 27.1 | 13.1 | 7.7 | 5.4 | 83.7 |
| | Jumbo | 2 | 5.8 | 0.2 | 1.9 | 81.3 | 3.1 | 0.1 | 1.1 | 2.2 | 2.5 | 0.2 | 1.8 | 26.2 | 13.1 | 7.8 | 5.4 | 83.9 |
| C458-1 Ave. | | | 6.1 | 0.2 | 1.9 | 80.2 | 3.5 | 0.1 | 1.0 | 2.3 | 2.7 | 0.2 | 1.8 | 23.0 | 13.4 | 8.0 | 5.5 | 82.9 |
| C458-5 | #1 | 1 | 6.2 | 0.1 | 2.0 | 77.6 | 4.5 | 0.8 | 1.1 | 2.3 | 3.0 | 0.3 | 1.9 | 17.2 | 14.2 | 8.7 | 6.0 | 80.4 |
| | #1 | 2 | 6.3 | 0.1 | 2.2 | 78.3 | 4.3 | 0.1 | 1.2 | 2.3 | 3.1 | 0.2 | 1.9 | 18.2 | 14.7 | 8.7 | 6.2 | 80.9 |
| | Medium | 1 | 5.9 | 0.1 | 1.9 | 80.0 | 3.4 | 0.3 | 1.1 | 2.3 | 2.8 | 0.2 | 1.9 | 23.5 | 13.6 | 8.3 | 5.8 | 82.6 |
| | Medium | 2 | 5.9 | 0.1 | 2.0 | 80.2 | 3.2 | 0.1 | 1.1 | 2.3 | 2.8 | 0.3 | 1.9 | 25.1 | 13.7 | 8.4 | 5.8 | 82.9 |
| | Jumbo | 1 | 5.7 | 0.1 | 1.7 | 81.0 | 3.1 | 0.1 | 1.1 | 2.3 | 2.7 | 0.2 | 1.9 | 26.1 | 13.1 | 8.2 | 5.7 | 83.6 |
| | Jumbo | 2 | 5.7 | 0.1 | 1.8 | 80.8 | 3.1 | 0.4 | 1.1 | 2.2 | 2.6 | 0.2 | 1.9 | 26.1 | 13.1 | 8.0 | 5.6 | 83.3 |
| C458-5 Ave. | | | 6.0 | 0.1 | 1.9 | 79.7 | 3.6 | 0.3 | 1.1 | 2.3 | 2.8 | 0.2 | 1.9 | 22.7 | 13.7 | 8.4 | 5.9 | 82.3 |
| C458 Ave. | #1 | | 6.3 | 0.2 | 2.0 | 78.7 | 4.1 | 0.3 | 1.1 | 2.4 | 2.9 | 0.3 | 1.9 | 19.2 | 14.1 | 8.5 | 5.8 | 81.5 |
| | Medium | | 6.0 | 0.1 | 1.9 | 80.1 | 3.5 | 0.2 | 1.1 | 2.3 | 2.8 | 0.2 | 1.9 | 23.0 | 13.5 | 8.2 | 5.7 | 82.7 |
| | Jumbo | | 5.8 | 0.1 | 1.8 | 81.1 | 3.1 | 0.2 | 1.1 | 2.2 | 2.6 | 0.2 | 1.9 | 26.4 | 13.1 | 7.9 | 5.5 | 83.6 |
| | All | | 6.0 | 0.1 | 1.9 | 79.9 | 3.6 | 0.2 | 1.1 | 2.3 | 2.7 | 0.2 | 1.9 | 22.8 | 13.6 | 8.2 | 5.7 | 82.6 |
| D596 | #1 | 1 | 6.4 | 0.2 | 2.1 | 78.1 | 5.3 | 0.0 | 1.1 | 2.1 | 2.7 | 0.2 | 1.7 | 14.7 | 14.0 | 7.8 | 5.5 | 80.6 |
| | #1 | 2 | 6.4 | 0.2 | 2.0 | 77.9 | 5.3 | 0.4 | 1.1 | 2.1 | 2.8 | 0.2 | 1.7 | 14.7 | 14.0 | 7.9 | 5.6 | 80.4 |
| | Medium | 1 | 6.1 | 0.2 | 2.1 | 79.0 | 4.6 | 0.2 | 1.1 | 2.1 | 2.6 | 0.2 | 1.8 | 17.2 | 13.7 | 7.8 | 5.5 | 81.5 |
| | Medium | 2 | 6.2 | 0.2 | 1.9 | 79.2 | 4.7 | 0.1 | 1.1 | 2.1 | 2.8 | 0.2 | 1.8 | 16.9 | 13.6 | 7.8 | 5.5 | 81.7 |
| | Jumbo | 1 | 6.0 | 0.2 | 1.8 | 79.3 | 4.5 | 0.4 | 1.0 | 2.1 | 2.6 | 0.2 | 1.8 | 17.6 | 13.2 | 7.7 | 5.4 | 81.8 |
| | Jumbo | 2 | 6.0 | 0.2 | 1.9 | 79.7 | 4.3 | 0.3 | 1.1 | 2.1 | 2.5 | 0.2 | 1.8 | 18.5 | 13.3 | 7.7 | 5.4 | 82.2 |
| D696 Ave. | #1 | | 6.4 | 0.2 | 2.1 | 78.0 | 5.3 | 0.2 | 1.1 | 2.1 | 2.8 | 0.2 | 1.7 | 14.7 | 14.0 | 7.9 | 5.6 | 80.5 |
| | Medium | | 6.2 | 0.2 | 2.0 | 79.1 | 4.7 | 0.2 | 1.1 | 2.1 | 2.6 | 0.2 | 1.8 | 17.0 | 13.7 | 7.8 | 5.5 | 81.6 |
| | Jumbo | | 6.0 | 0.2 | 1.9 | 79.5 | 4.4 | 0.4 | 1.1 | 2.1 | 2.6 | 0.2 | 1.8 | 18.1 | 13.3 | 7.7 | 5.4 | 82.0 |
| | All | | 6.2 | 0.2 | 2.0 | 78.7 | 4.9 | 0.2 | 1.1 | 2.1 | 2.7 | 0.2 | 1.8 | 16.2 | 13.7 | 7.8 | 5.5 | 81.2 |
| Florunner check | | 1 | 10.3 | 0.2 | 2.7 | 55.2 | 23.9 | 0.1 | 1.4 | 1.4 | 2.9 | 0.1 | 1.7 | 2.3 | 19.0 | 7.5 | 6.0 | 56.9 |
| Florunner check | | 2 | 10.5 | 0.1 | 2.5 | 54.7 | 24.6 | 0.1 | 1.4 | 1.4 | 2.9 | 0.1 | 1.7 | 2.2 | 19.0 | 7.5 | 6.0 | 56.3 |
| Florunner ave. | | | 10.4 | 0.2 | 2.6 | 55.0 | 24.3 | 0.1 | 1.4 | 1.4 | 2.9 | 0.1 | 1.7 | 2.3 | 19.0 | 7.5 | 6.0 | 56.6 |

G. 1994 Peanut Trials

Yield results from 1994 peanut trials confirm the agronomic similarity of C458 and D596 with Florunner (Table 5), as well as the remarkably improved fatty acid profile (Table 6). In addition, peanuts from the 1994 Davisboro, Ga. trial site were sized, crushed, and analyzed. The oil crush was carried out using a Carver press at 16,000 psig. After threshing, the peanuts were sized to medium or jumbo. (Medium runners will pass through a 18/64"×3/4" slotted screen and will not pass through a 16/64"×3/4" slotted screen, while jumbo runners will not pass through a 18/64"×3/4" screen.) Oil from the crush was analyzed in accordance with While the previous fatty acid data presented herein has been obtained using solvent extraction, which can result in the presence of extraneous fatty acids (such as from membrane lipids), the crush data (Table 7) is a more accurate indication of the fatty acid profile of commercial products incorporating peanuts or peanut products of the present invention.

(In the tables herein, the column heading "20+" indicates the percentage of all fatty acids having 20 or more carbons; "20:0+" indicates the percentage of all saturated fatty acids having 20 or more carbons; and "XX:1" indicates the percentage of all monounsaturated fatty acids.)

TABLE 5

Comparative Yield Results
1994 Peanut Trials

| Entry | Perry Early (lbs/acre) | Perry Early (% Flo) | Perry Late (lbs/acre) | Perry Late (% Flo) | Davisboro (lbs/acre) | Davisboro (% Flo) | Average (lbs/acre) | Average (% Flo) |
|---|---|---|---|---|---|---|---|---|
| Florunner | 3957 | 100 | 3185 | 100 | 2532 | 100 | 3225 | 100 |
| GK-7 | 3585 | 91 | 3388 | 106 | 2426 | 96 | 3133 | 97 |
| Georgia Runner | 3930 | 99 | 3131 | 98 | 2514 | 99 | 3192 | 99 |
| C458-1 | 3712 | 94 | 3222 | 101 | 2505 | 99 | 3146 | 98 |
| C458-3 | 3657 | 92 | 2623 | 82 | 2638 | 104 | 2973 | 92 |
| C458-4 | 3530 | 89 | 3176 | 100 | 1960 | 77 | 2889 | 90 |
| C458-5 | 3159 | 80 | 3013 | 95 | 2468 | 97 | 2880 | 89 |
| C458-6 | 3494 | 88 | 3113 | 98 | 2878 | 114 | 3162 | 98 |
| C458-8 | 3439 | 87 | 3008 | 94 | 2283 | 90 | 2910 | 90 |
| D596-3 | 3802 | 96 | | | | | | |
| Mean | 3627 | | 3095 | | 2467 | | | |
| CV (%) | 9.2 | | 10.9 | | 14.9 | | | |
| Planted | 5/13/94 | | 5/27/94 | | 5/20/94 | | | |
| Dug | 10/5/94 | | 10/5/94 | | 10/21/94 | | | |
| Threshed | 10/18/94 | | 10/18/94 | | 10/27/94 | | | |

TABLE 6

Fatty Acid Profiles;
1994 Georgia Isoblocks

| Cultivar | Seed size | Sample | 16:0 | 16:1 | 18:0 | 18:1 | 18:2 | 18:3 | 20:0 | 20:1 | 22:0 | 22:1 | 24:0 | O/L | Sats | 20+ | 20:0+ | XX:1 |
|---|---|---|---|---|---|---|---|---|---|---|---|---|---|---|---|---|---|---|
| C458-1 | Medium | 1 | 5.6 | 0.1 | 1.8 | 79.0 | 3.9 | 0.1 | 1.1 | 2.7 | 3.2 | 0.3 | 2.1 | 20.3 | 13.8 | 9.4 | 6.4 | 82.1 |
| C458-1 | Medium | 2 | 5.4 | 0.1 | 1.8 | 79.6 | 3.3 | 0.1 | 1.1 | 2.7 | 3.3 | 0.3 | 2.2 | 24.1 | 13.8 | 9.6 | 6.6 | 82.7 |
| Average | | | 5.5 | 0.1 | 1.8 | 79.3 | 3.6 | 0.1 | 1.1 | 2.7 | 3.3 | 0.3 | 2.2 | 22.0 | 13.9 | 9.6 | 6.6 | 82.4 |
| C458-5 | Medium | 1 | 5.8 | 0.1 | 2.2 | 77.5 | 4.1 | 0.1 | 1.3 | 2.7 | 3.5 | 0.3 | 2.3 | 18.9 | 15.1 | 10.1 | 7.1 | 80.6 |
| C458-5 | Medium | 2 | 5.5 | 0.1 | 2.0 | 78.9 | 3.6 | 0.1 | 1.2 | 2.7 | 3.4 | 0.3 | 2.2 | 21.9 | 14.3 | 9.8 | 6.8 | 82.6 |
| Average | | | 5.7 | 0.1 | 2.1 | 78.2 | 3.9 | 0.1 | 1.3 | 2.7 | 3.5 | 0.3 | 2.3 | 20.1 | 14.9 | 10.1 | 7.1 | 81.3 |
| Florunner check | | 1 | 9.3 | 0.1 | 2.1 | 49.2 | 30.9 | 0.1 | 1.3 | 1.6 | 3.3 | 0.1 | 2.0 | 1.6 | 18.0 | 8.3 | 6.6 | 51.0 |
| Florunner check | | 2 | 9.0 | 0.1 | 2.1 | 50.6 | 29.7 | 0.1 | 1.3 | 1.7 | 3.3 | 0.1 | 2.0 | 1.7 | 17.7 | 8.4 | 6.6 | 52.0 |
| Average | | | 9.2 | 0.1 | 2.1 | 49.9 | 30.3 | 0.1 | 1.3 | 1.7 | 3.3 | 0.1 | 2.0 | 1.6 | 17.9 | 8.4 | 6.6 | 51.8 |

Each profile is based on a sample of 20 seeds

TABLE 7

Oil Crush Results
1994 Davisboro, Georgia Peanut Trial

| Cultivar | Seed size | Sample | 16:0 | 16:1 | 18:0 | 18:1 | 18:2 | 18:3 | 20:0 | 20:1 | 22:0 | 22:1 | 24:0 | O/L | Sats | 20+ | 20:0+ | XX:1 |
|---|---|---|---|---|---|---|---|---|---|---|---|---|---|---|---|---|---|---|
| C458-1 | Medium | 1 | 5.2 | 0.1 | 2.2 | 80.1 | 4.6 | tr | 1.1 | 2.0 | 2.7 | 0.2 | 1.8 | 17.4 | 13.0 | 7.8 | 5.6 | 82.4 |
| | Medium | 2 | 5.3 | 0.1 | 2.1 | 80.0 | 4.6 | tr | 1.1 | 2.0 | 2.6 | 0.2 | 1.7 | 17.4 | 12.9 | 7.6 | 5.4 | 82.3 |
| | Average | | 5.3 | 0.1 | 2.2 | 80.1 | 4.6 | tr | 1.1 | 2.0 | 2.7 | 0.2 | 1.8 | 17.4 | 12.9 | 7.7 | 5.5 | 82.3 |
| | Jumbo | 1 | 5.0 | 0.1 | 2.2 | 82.1 | 3.0 | tr | 1.1 | 2.0 | 2.6 | 0.2 | 1.7 | 27.1 | 12.5 | 7.5 | 5.3 | 84.3 |
| | Jumbo | 2 | 4.9 | 0.1 | 2.2 | 81.7 | 3.2 | tr | 1.1 | 2.0 | 2.8 | 0.2 | 1.7 | 25.5 | 12.5 | 7.5 | 5.4 | 83.9 |
| | Average | | 5.0 | 0.1 | 2.2 | 81.9 | 3.1 | tr | 1.1 | 2.0 | 2.6 | 0.2 | 1.7 | 26.2 | 12.5 | 7.5 | 5.4 | 84.1 |
| GK-7 | | 1 | 8.8 | 0.2 | 2.0 | 52.6 | 28.5 | tr | 1.1 | 1.5 | 3.0 | 0.1 | 1.8 | 1.8 | 16.7 | 7.6 | 5.9 | 54.4 |
| | | 2 | 8.8 | 0.1 | 2.0 | 52.6 | 28.6 | tr | 1.1 | 1.5 | 3.0 | 0.1 | 1.8 | 1.8 | 16.7 | 7.6 | 5.9 | 54.4 |
| | Average | | 8.8 | 0.1 | 2.0 | 52.6 | 28.6 | tr | 1.1 | 1.5 | 3.0 | 0.1 | 1.8 | 1.8 | 16.7 | 7.6 | 5.9 | 54.4 |
| C458-1 | | 1 | 5.1 | 0.1 | 1.8 | 81.8 | 3.2 | tr | 1.0 | 2.1 | 2.8 | 0.2 | 1.7 | 25.7 | 12.4 | 7.8 | 5.5 | 84.3 |
| | | 2 | 5.1 | 0.1 | 1.8 | 81.8 | 3.2 | tr | 1.0 | 2.2 | 2.8 | 0.2 | 1.8 | 25.7 | 12.4 | 7.9 | 5.5 | 84.1 |
| | Average | | 5.1 | 0.1 | 1.8 | 81.7 | 3.2 | tr | 1.0 | 2.1 | 2.8 | 0.2 | 1.8 | 25.7 | 12.4 | 7.9 | 5.5 | 84.2 |
| Florunner | | 1 | 8.8 | 0.2 | 2.0 | 51.6 | 29.7 | tr | 1.1 | 1.4 | 3.0 | 0.1 | 1.7 | 1.7 | 16.6 | 7.3 | 5.8 | 53.4 |
| | | 2 | 8.9 | 0.1 | 2.0 | 51.7 | 29.7 | tr | 1.1 | 1.4 | 3.0 | 0.1 | 1.7 | 1.7 | 16.6 | 7.3 | 5.8 | 53.4 |
| | Average | | 8.8 | 0.1 | 2.0 | 51.7 | 29.8 | tr | 1.1 | 1.4 | 3.0 | 0.1 | 1.7 | 1.7 | 16.6 | 7.3 | 5.8 | 53.3 |
| Planters Peanut Oil | | 1 | 9.7 | 0.1 | 2.4 | 50.2 | 29.6 | tr | 1.2 | 1.4 | 3.3 | 0.1 | 1.7 | 1.7 | 18.3 | 7.8 | 6.2 | 51.9 |
| | | 2 | 9.8 | 0.1 | 2.4 | 50.2 | 29.6 | tr | 1.2 | 1.4 | 3.2 | 0.1 | 1.7 | 1.7 | 18.3 | 7.7 | 6.1 | 51.9 |
| | Average | | 9.7 | 0.1 | 2.4 | 50.2 | 29.6 | tr | 1.2 | 1.4 | 3.2 | 0.1 | 1.7 | 1.7 | 18.3 | 7.7 | 6.2 | 51.9 |

The crushed oil from C458-5 contained about 80–82% oleic acid, 3–4.6% linoleic acid (yielding an O/L ratio value range of 17.4–27.3), and about 5–5.3% palmitic acid. In comparison, Florunner crush oil contained less than 52% oleic acid, 29.75% linoleic acid (yielding an O/L ratio value of only 1.73), and 8.83% palmitic acid. The C458-5 crush oil may also be contrasted with Planter Peanut oil, another industry standard, which contains about 50.2% oleic acid, 29.6% linoleic acid (for an O/L ratio value of about 1.7), and 9.7% palmitic acid.

It should be noted that oil profile can be affected by environmental factors, primarily the growing temperature, the length of the growing season, and the timing and amount of watering received. These factors can cause relatively minor variation in oil profile, and it should be understood that these fall within the scope of the present invention.

The following Table 8 presents a summary further evidencing the results achieved by the present invention.

Leaflet length/width ratio: 2.37
5. POD: (Average for 20 pods at maturity)
  Length: 28 mm.
  Diameter: 13 mm.
  Number of seeds per pod: 2
  Surface: 1=Glabrous (Florunner)

TABLE 8

Summary

| Source | Cultivar | 16:0 | 16:1 | 18:0 | 18:1 | 18:2 | 18:3 | 20:0 | 20:1 | 22:0 | 22:1 | 24:0 | O/L | Sats | 20+ | 20:0+ | XX:1 |
|---|---|---|---|---|---|---|---|---|---|---|---|---|---|---|---|---|---|
| 92-93 PR | C458-1 | 6.5 | 0.1 | 2.2 | 77.3 | 4.9 | 0.1 | 1.1 | 2.5 | 3.1 | 0.3 | 1.9 | 15.8 | 14.8 | 9.0 | 6.1 | 80.3 |
|  | C458-3 | 5.5 | 0.1 | 2.5 | 79.5 | 3.5 | 0.1 | 1.3 | 2.3 | 3.0 | 0.3 | 2.1 | 22.9 | 14.3 | 8.8 | 6.3 | 82.2 |
|  | C458-4 | 5.6 | 0.1 | 1.7 | 79.8 | 3.7 | 0.1 | 1.0 | 2.7 | 3.0 | 0.3 | 2.1 | 21.6 | 13.5 | 9.1 | 6.2 | 82.8 |
|  | C458-5 | 5.4 | 0.1 | 1.8 | 80.7 | 3.1 | 0.1 | 1.1 | 2.5 | 3.0 | 0.3 | 2.2 | 26.2 | 13.4 | 9.0 | 6.3 | 83.5 |
|  | C458-6 | 5.9 | 0.2 | 1.7 | 79.7 | 3.4 | 0.1 | 1.1 | 2.5 | 3.1 | 0.3 | 2.1 | 23.4 | 13.9 | 9.0 | 6.3 | 82.6 |
|  | C458-8 | 7.0 | 0.1 | 2.4 | 75.0 | 5.5 | 0.1 | 1.3 | 2.5 | 3.7 | 0.3 | 2.1 | 13.6 | 16.5 | 10.0 | 7.1 | 77.9 |
|  | C458 Ave. | 6.0 | 0.1 | 2.0 | 78.6 | 4.0 | 0.1 | 1.1 | 2.5 | 3.1 | 0.3 | 2.1 | 20.6 | 14.4 | 9.1 | 6.4 | 81.5 |
| Control | C457 | 10.1 | 0.1 | 2.2 | 48.4 | 32.1 | 0.1 | 1.2 | 1.6 | 3.3 | 0.1 | 1.9 | 1.5 | 18.7 | 8.0 | 6.3 | 50.2 |
|  | C459 | 10.1 | 0.1 | 2.0 | 46.7 | 33.2 | 0.1 | 1.2 | 1.7 | 3.4 | 0.2 | 1.9 | 1.4 | 18.6 | 8.3 | 6.5 | 48.6 |
| 93 GA | C458-1 | 5.2 | 0.0 | 1.1 | 80.5 | 4.6 | 0.1 | 1.0 | 2.8 | 2.6 | 0.4 | 1.7 | 17.5 | 11.6 | 8.5 | 5.3 | 83.7 |
|  | C458-3 | 5.1 | 0.1 | 1.9 | 82.4 | 3.3 | 0.1 | 1.0 | 2.5 | 2.6 | 0.3 | 0.7 | 25.0 | 11.3 | 7.1 | 4.3 | 85.3 |
|  | C458-4 | 5.0 | 0.1 | 1.7 | 81.0 | 3.7 | 0.1 | 0.9 | 2.9 | 2.8 | 0.4 | 1.4 | 21.9 | 11.8 | 8.4 | 5.1 | 84.4 |
|  | C458-5 | 5.1 | 0.1 | 2.0 | 81.0 | 3.3 | 0.1 | 1.1 | 2.7 | 2.8 | 0.3 | 1.5 | 24.5 | 12.5 | 8.4 | 5.4 | 84.1 |
|  | C458-6 | 4.9 | 0.1 | 1.7 | 81.2 | 3.3 | 0.1 | 1.0 | 2.8 | 2.7 | 0.4 | 1.8 | 24.6 | 12.1 | 8.7 | 5.5 | 84.5 |
|  | C458-8 | 5.0 | 0.1 | 1.8 | 79.0 | 4.6 | 0.1 | 1.1 | 3.3 | 3.0 | 0.5 | 1.5 | 17.2 | 12.4 | 9.4 | 5.6 | 82.9 |
|  | C458 Ave. | 5.1 | 0.1 | 1.7 | 80.9 | 3.8 | 0.1 | 1.0 | 2.8 | 2.8 | 0.4 | 1.4 | 21.8 | 12.0 | 8.4 | 5.2 | 84.2 |
| Control | C458-2 | 9.2 | 0.1 | 2.0 | 45.8 | 34.7 | 0.1 | 1.3 | 1.6 | 3.3 | 0.1 | 1.8 | 1.3 | 17.6 | 8.1 | 6.4 | 47.6 |
|  | Florunner | 8.9 | 0.1 | 2.1 | 48.2 | 32.5 | 0.1 | 1.3 | 1.6 | 3.1 | 0.1 | 2.0 | 1.5 | 17.4 | 8.1 | 6.4 | 50.0 |
| 93-94 PR | C458-1 | 6.0 | 0.1 | 1.8 | 80.5 | 3.4 | 0.1 | 1.0 | 2.3 | 2.7 | 0.2 | 1.9 | 23.7 | 13.4 | 8.1 | 5.6 | 83.1 |
|  | C458-3 | 6.0 | 0.0 | 1.7 | 81.1 | 3.5 | 0.1 | 1.0 | 2.4 | 2.9 | 0.2 | 1.1 | 23.2 | 12.7 | 7.6 | 5.0 | 83.7 |
|  | C458-4 | 6.0 | 0.1 | 1.7 | 80.3 | 3.6 | 0.1 | 1.0 | 2.4 | 2.8 | 0.3 | 1.7 | 22.3 | 13.2 | 8.2 | 5.5 | 83.1 |
|  | C458-5 | 6.1 | 0.1 | 1.9 | 80.8 | 3.3 | 0.1 | 1.1 | 2.3 | 2.8 | 0.2 | 1.3 | 24.5 | 13.2 | 7.7 | 5.2 | 83.4 |
|  | C458-6 | 6.0 | 0.1 | 1.6 | 80.8 | 3.8 | 0.1 | 1.0 | 2.5 | 2.9 | 0.3 | 0.9 | 21.3 | 12.4 | 7.6 | 4.8 | 83.7 |
|  | C458-8 | 6.1 | 0.0 | 1.9 | 80.8 | 3.5 | 0.1 | 1.0 | 2.3 | 2.5 | 0.3 | 1.5 | 23.1 | 13.0 | 7.6 | 5.0 | 83.4 |
|  | C458 Ave. | 6.0 | 0.1 | 1.8 | 80.7 | 3.5 | 0.1 | 1.0 | 2.4 | 2.8 | 0.3 | 1.4 | 23.0 | 13.0 | 7.8 | 5.2 | 83.4 |
|  | D596-3 | 6.0 | 0.1 | 1.9 | 80.2 | 4.2 | 0.1 | 1.1 | 2.0 | 2.6 | 0.1 | 1.7 | 19.1 | 13.3 | 7.5 | 5.4 | 82.4 |
| 93-94 PR | C458-1 | 6.1 | 0.2 | 1.9 | 80.2 | 3.5 | 0.1 | 1.0 | 2.3 | 2.7 | 0.2 | 1.8 | 20.8 | 14.4 | 8.0 | 5.5 | 82.9 |
| (incr.) | C458-5 | 6.0 | 0.1 | 1.9 | 79.7 | 3.6 | 0.3 | 1.1 | 2.3 | 2.8 | 0.2 | 1.9 | 22.7 | 13.7 | 8.4 | 5.9 | 82.3 |
|  | D596 | 6.2 | 0.2 | 2.0 | 78.7 | 4.9 | 0.2 | 1.1 | 2.1 | 2.7 | 0.2 | 1.8 | 16.2 | 13.7 | 7.8 | 5.5 | 81.2 |
|  | Florunner | 10.4 | 0.2 | 2.6 | 55.0 | 24.3 | 0.1 | 1.4 | 1.4 | 2.9 | 0.1 | 1.7 | 2.3 | 19.0 | 7.5 | 6.0 | 56.6 |
| 94 GA | C458-1 | 5.5 | 0.1 | 1.8 | 79.3 | 3.6 | 0.1 | 1.1 | 2.7 | 3.3 | 0.3 | 2.2 | 22.0 | 13.9 | 9.6 | 6.6 | 82.4 |
|  | C458-5 | 5.7 | 0.1 | 2.1 | 78.2 | 3.9 | 0.1 | 1.3 | 2.7 | 3.5 | 0.3 | 2.3 | 20.1 | 14.9 | 10.1 | 7.1 | 81.3 |
|  | Florunner | 9.2 | 0.1 | 2.1 | 49.9 | 30.3 | 0.1 | 1.3 | 1.7 | 3.3 | 0.1 | 2.0 | 1.6 | 17.9 | 8.4 | 6.6 | 51.8 |

C458-1 and C458-5 thus appear identical to Florunner in all characteristics other than seed lipid composition, with C458-1 having the better agronomic characteristics, especially in yield. Based on the other fatty acid analyses, crush oil from C458-1 would be expected to be comparable to that from C458-5. Table 9 presents an objective description of C458, which should be applicable to D596 as well.

TABLE 9

Objective Description of C458
1. BOTANICAL TYPE
  Flowering on the Main Stem: Absent
  Branching Pattern: Alternate—Pairs of vegetative & reproductive branches (Virginia)
2. PLANT
  Habit Prostrate (Florunner)
  Branching: Profuse (Florunner)
3. MATURITY
  Region: S.E. United States
  Number of days to maturity: 150
  Days earlier than Florunner: 0
  Days later than Florunner: 0
4. LEAVES
  Leaflet length: 28 mm.

Beak: Inconspicuous
6. SEED (Mature, cured but not aged)
  Coat color: Red
  Coat surface: Smooth
  Shape: Short-broad (Florunner)
  Length: 15 mm.
  Width: 9 mm.
  Grams per 100 seed (8% moisture): 70
7. COMPARISON WITH ONE OR MORE SIMILAR VARIETIES
  Present Variety: Oleic:Linoleic Acid Ratio=26.2
  Florunner 1.5
8. VARIETY WHICH MOST CLOSELY RESEMBLES THAT SUBMITTED
  Florunner most closely resembles the present variety in pod color, seedling vigor, seed dormancy, hull thickness, seed size, and leaf color.
  (The parenthetical varietal names represent those varieties commonly used as benchmarks for the characteristics indicated.)

It should be emphasized that the present invention does not relate merely to the isolation of a particularly desirable fatty acid genotype, which would require a prolonged breeding/backcrossing program and/or acceptance of compromised agronomic and processing characteristics in order to become commercially viable. Rather, the present invention is commercial in its present form.

Seed from the varieties of the present invention are suitable for use in either industrial or food applications. In industrial applications the seed may be crushed for the oil which, due to its low polyunsaturate content, would have improved oxidative stability in addition to offering biodegradablity. The oil could, depending on the intended environment of use, be used as is, or in conjunction with any one or more of various standard additives, e.g., extreme-pressure and anti-wear agents, oxidation and thermal-stability improvers, corrosion-inhibitors, viscosity-index improvers, pour point and/or floc point depressants, dispersants, antifoaming agents, viscosity adjusters, metal deactivators, acid acceptors, etc.

In food applications the oil could also be used; or the seed itself, whole or reduced, could be used as, or incorporated into, an edible substance. Salted or unsalted nuts (shelled and unshelled); peanut butters; candies, cookies, and other desserts (including frozen desserts) and confectionaries, and in general all peanut/peanut oil-containing comestibles, containing the whole or any part of the seeds of the present invention will exhibit improved shelf life and the consequent sensory advantages inherent in the oil profile of the seed oil.

The present invention has of necessity been discussed herein by reference to certain specific methods and materials. The enumeration of these methods and materials was merely illustrative, and in no way constitutes any limitation on the scope of the present invention. It is to be expected that those skilled in the art may discern and practice variations of or alternatives to the specific teachings provided herein, without departing from the scope of the present invention.

What we claim is:

1. A Virginia-type *Arachis hypogaea* L. Runner peanut plant having seed containing oil having an oleic acid content of at least about 77.5%, and a palmitic acid content of 6.4% or less, produced by the process of:

treating a plurality of Virginia-type Runner peanut seed with an alkylating mutagen;

culturing said seeds under conditions whereby plants are obtained from said seeds;

harvesting seed from said plants;

analyzing said harvested seeds for fatty acid content;

identifying harvested seed having a high oleic acid content from those analyzed;

culturing said identified seed under conditions whereby plants are produced;

harvesting seed from said plants;

analyzing said harvested seed for fatty acid content;

identifying harvested seed having an oleic acid content of at least 77.5%, and a palmitic acid content of 6.4% or less; and culturing said identified seed under conditions whereby a plant is produced, said plant yielding seed having an oleic acid content of at least 77.5%, and a palmitic acid content of 6.4% or less.

2. The plant of claim 1, said seed further having a linoleic acid content of from about 2.8% to about 5.3%.

3. The plant according to claim 2, wherein said linoleic acid content is from about 2.8% to about 4.9%.

4. The plant of claim 2, wherein said linoleic acid content is from about 4.2% to about 5.3%.

5. The plant according to claim 1, wherein said palmitic acid content is 6.0% or less.

6. The plant according to claim 3, wherein said palmitic acid content is 6.0% or less.

7. A seed of the plant of claim 1, said seed having an oleic acid content of from about 77.5% to about 82.4% and a palmitic acid content of 6.4% or less.

8. A seed according to claim 7, further having a linoleic acid content of from about 2.8% to about 5.3%.

9. A seed according to claim 7, further having a linoleic acid content of from about 2.8%. to about 4.9%.

10. A seed according to claim 7, further having a linoleic acid content of from about 4.2% to about 5.3%.

11. A seed according to claim 8, further having a palmitic acid content of 6.0% or less.

12. A seed according to claim 9, further having a palmitic acid content of 6.0% or less.

13. The Virginia-type Runner peanut plant of claim 1, wherein said alkylating mutagen is ethyl methane sulfonate.

14. A Virginia-type Runner peanut plant produced by growing the seed of claim 7, whereby said plant produces seeds having an oleic acid content of at least 77.5%, and a palmitic acid content of 6.4% or less.

15. A Virginia-type Runner peanut decendant of the plant of claim 14, said decendant having seeds having an oleic acid content of at least 77.5%, and a palmitic acid content of 6.4% or less.

16. The Virginia-type runner peanut plant of claim 1, wherein said oleic acid content is from about 77.5% to about 82.4%.

17. The Virginia-type runner peanut plant of claim 13, wherein said palmitic acid content is 6.0% or less.

18. Seed of the plant of claim 13.

19. Seed of the plant of claim 16.

20. Seed of the plant of claim 17.

* * * * *

UNITED STATES PATENT AND TRADEMARK OFFICE
CERTIFICATE OF CORRECTION

PATENT NO. : 5,948,954                                Page 1 of 2
DATED : September 7, 1999
INVENTOR(S) : Michael Eugene Horn, Eric Jon Eikenberry, Juan Enrigue Romero Lanuza, James Douglas Sutton It is certified that error appears in the above-identified patent and that said Letters Patent is hereby corrected as shown below:

Column 1,
Line 5: "08/363,499, filed Dec. 23, 1994." should read -- 08/363,449, filed December 22, 1994. --

Column 7-8,
Table 1, Plant C458-1, Seed 4, Col. 20:0: "1.1" should read -- 1.2 --.

Columns 9-10,
Table 2, Plant 459-3, Seed 2, Col. O/L: "2.2" should read -- 1.2 --.
Table 3, Genotype C458-8, Column O/L: "11.2" should read -- 17.2 --.

Column 9,
Line 20: "1992-93" should read -- D. 1992-93 --.

Columns 11-12, Table 4B,
Cultivar C458-5, Seed #1, Sample 1, Column 20:1: "2.3"
should read -- 2.4 --.
Cultivar D596, Seed size Medium, Sample 2, Col. 22:0: "2.8" should read -- 2.6 --.

UNITED STATES PATENT AND TRADEMARK OFFICE
CERTIFICATE OF CORRECTION

PATENT NO.   : 5,948,954
DATED        : September 7, 1999
INVENTOR(S)  : Michael Eugene Horn, Eric Jon Eikenberry, Juan Enrigue Romero Lanuza, James Douglas Sutton It is certified that error appears in the above-identified patent and that said Letters Patent is hereby corrected as shown below:

Columns 13-14, Table 6,
Cultivar C458-5, Seed Medium, Sample 2, Col. XX:1: "82.6" should read -- 82.0 --.
Cultivar Florunner, Sample 2, Col. XX:1: "52.0" should read -- 52.5 --.

Columns 13-14, Table 7, Cultivar C 458-1,
Seed Jumbo, Sample 2, Col. 22:0: "2.8" should read -- 2.6 --.
Sample 2, Col. 18:1: "81.8" should read -- 81.6 --.

Column 15,
Line 58: "Habit" should read -- Habit: --.

Column 18,
Line 11: "to claim 2" should read -- to claim 1 --.

Signed and Sealed this

Seventh Day of August, 2001

*Attest:*

NICHOLAS P. GODICI
*Attesting Officer*   *Acting Director of the United States Patent and Trademark Office*